US005962312A

United States Patent [19]
Plowman et al.

[11] Patent Number: 5,962,312
[45] Date of Patent: Oct. 5, 1999

[54] DIAGNOSIS AND TREATMENT OF AUR-1 AND/OR AUR-2 RELATED DISORDERS

[75] Inventors: Gregory Plowman, San Carlos, Calif.; Kevin Mossie, Gauteng, South Africa

[73] Assignee: Sugen, Inc., Redwood City, Calif.

[21] Appl. No.: 08/755,728

[22] Filed: Nov. 25, 1996

Related U.S. Application Data

[60] Provisional application No. 60/008,809, Dec. 18, 1995, abandoned, and provisional application No. 60/023,943, Aug. 14, 1996, abandoned.

[51] Int. Cl.$^6$ ............................. C12N 15/63; C07H 21/04
[52] U.S. Cl. ................... 435/320.1; 536/23.2; 536/24.31
[58] Field of Search ............................... 435/320.1, 194; 536/23.2, 24.31

[56] References Cited

U.S. PATENT DOCUMENTS

| 4,945,050 | 7/1990 | Sanford et al. ....................... 435/172.1 |
| 5,283,173 | 2/1994 | Fields et al. ................................. 435/6 |

FOREIGN PATENT DOCUMENTS

| 9214748 | 9/1992 | WIPO . |
| 9423039 | 10/1994 | WIPO . |
| 9634985 | 7/1996 | WIPO . |

OTHER PUBLICATIONS

Kimura et al., "Molecular Cloning of a human homolog of Aurora, a serine/threonine kinase which regulates the chromosome segregation," Nippon Bunshi Seibutsu Gakkai Nenkai Puroguramu (1995), vol. 18, p. 497, Abst. 3P–205, 1995.
Kimura et al., "Cell Cycle–dependent Expression and Spindle Pole Localization of a Novel Human Protein Kinase, Aik, Related to Aurora of Drosophila and Yeast lpl1," J. Biol. Chem., vol. 272, No. 21, pp. 13766–13771, May 23, 1997.
Alberts, B. et al. 'Molecular Biology of the Cell,' Second Edition, published 1989, by Garland Publishing (New York), pp. 265–266, 1989.
Hillier, L. et al., EST Databases, Accession number R97911, available Sep. 11, 1995.
Hillier, L. et al., EST Databases, Accession number T36134, available Sep. 6, 1995.
Glover et al., "Mutations in aurora Prevent Centrosome Separation Leading to the Formation of Monopolar Spindles," Cell 81:95–105 (1995).
Hillier et al., "yq61f04.s1 Homo sapiens cDNA clone 200287 3"," EMBL Sequence Database, Heidelberg, Brd., XP002029128, accession no. R97724, Oct. 1, 1995.
Hillier et al., "y60d11.s1 Homo sapiens cDNA clone 200181 3" similar to SP:S34642 S34642 Hypothetical Protein—African Clawed Frog," EMBL Sequence Database, Heidelberg, Brd., XP002029129, accession no. R97912, Oct. 1, 1995.

Mossie et al., "Colon carcinoma kinase–4 defines a new subclass of the receptor tyrosine kinase family," Oncogene 11(10):2179–2184 (1995).
Roghi et al., "Xenopus Iaevis mRNA encoding protein kinase," EMBL Sequence Database, Heidelberg, Brd., XP002029130, accession no. Z17206, Jan. 1, 1995.
Roghi et al., "Xenopus Iaevis mRNA encoding protein kinase," EMBL Sequence Database, Heidelberg, Brd., XP002029131, accession no. Z17207, Jan. 1, 1995.
Hammer et al., "Spontaneous Inflammatory Disease in Transgenic Rats Expressing HLA–B27 and Human $\beta_2$m: An Animal Model of HLA–B27–Associated Human Disorders," Cell 63:1009–1112 (1990).
Houdebine and Chourrout, "Transgenesis in Fish," Experientia 47:891–897 (1991).
Johnston and Hopper, "Isolation of the yeast regulatory gene GLA4 and analysis of its dosage effects on the galactose/melibiose regulon," Proc. Natl. Acad. Sci. USA 79:6971–6975 (1982).
Joyner et al., "Production of a mutation in mouse En–2 gene by homologous recombination in embryonic stem cells," Nature 338:153–156 (1989).
Liu et al., "Construction of a GAL1–Regulated Yeast cDNA Expression Library and its Application to the Identification of Genes Whose Overexpression Causes Lethality in Yeast," Genetics 132:665–673 (1992).
McKnight, "Functional Relationships between Transcriptional Control Signals of the Thymidine Kinase Gene of Herpes Simplex Virus," Cell 31:355–365 (1982). 2
Miller and Rosman, "Improved Retroviral Vectors for Gene Transfer and Expression," BioTechniques 7(9):982–990 (1989).
Miller, "Human gene therapy comes of age," Nature 357:455–460 (1992).
Mulligan, "The Basic Science of Gene Therapy," Science 260:926–932 (1993).
Nelson, "Detection of Acridinium Esters by Chemiluminescence," Nonisotopic DNA Probe Techniques, ed. Larry J. Kricka, (San Diego: Academic Press, Inc.) pp. 275–310 (1992).
Pursel et al., "Genetic Engineering of Livestock," Science 244:1281–1288 (1989).
Redemann et al., "Anti–Oncogenic Activity of Signalling–Defective Epidermal Growth Factor Receptor Mutants," Molecular and Cellular Biology 12(2):491–498 (1992).

(List continued on next page.)

Primary Examiner—Kawai Lau
Attorney, Agent, or Firm—Lyon & Lyon LLP

[57] ABSTRACT

The present invention relates to AUR-1 and/or AUR-2 polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for AUR-1 and/or AUR-2 related diseases or conditions characterized by an abnormal interaction between a AUR-1 and/or AUR-2 polypeptide and a AUR-1 and/or AUR-2 binding partner.

20 Claims, No Drawings

OTHER PUBLICATIONS

Silver et al., "Amino terminus of the yeast GAL4 gene product is sufficient for nuclear localization," *Proc. Natl. Acad. Sci. USA* 81:5951–5955 (1984).

Southern, "Detection of Specific Sequences Among DNA Fragments Separated by Gel Electrophoresis," *J. Mol. Biol.* 98:503–517 (1975).

Tabor et al., "DNA sequence analysis with a modified bacteriophage T7 DNA polymerase," *Proc. Natl. Acad. Sci. USA* 84:4767–4771 (1987).

Yang et al., "In Vivo and In Vitro Gene Transfer to Mammalian Somatic Cells by Particle Bombardment," *Proc. Natl. Acad. Sci. USA* 87:9568–9572 (1990).

Abe et al., "Molecular Characterization of a Novel Metabotropic Glutamate Receptor mGluR5 Coupled to Inositol Pohosphate/$Ca^{2+}$ Signal," *J. Biol. Chem.* 267(19):13361–13368 (1992).

Altschul et al., "Basic Local Alignment Search Tool," *J. Mol. Biol.* 215:403–410 (1990).

Benoist and Chambon, "in vivo sequence requirements of the SV40 early promoter region," *Nature* 290:304–310 (1981).

Brinster et al., "Factors Affecting the Efficiency of Introducting Foreign DNA into Mice by Microinjecting Eggs," *Proc. Natl. Acad. Sci. USA* 82:4438–4442 (1995).

Capecchi, "Altering the Genome by Homologous Recombination," *Science* 244:1288–1292 (1989).

Chan and Botstein, "Isolated and Characterization of Chromosome–Gain and Increase–in–Ploidy Mutants in Yeast," *Genetics* 135:677–691 (1993).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Francisco et al., "Type 1 Protein Phosphatase Acts in Opposition to IPl1 Protein Kinase in Regulating Yeast Chromosome Segregation," *Molecular and Cellular Biology* 14(7):4731–4740 (1994).

Gottesman, "Bacterial Regulation: Global Regulatory Networks," *Ann. Rev. Genet.* 18:415–441 (1984).

Hamer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).

ID NO:4.

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 1244 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (xi) SEQUENCE DESCRIPTION: SEQ ID NO: 1:

```
CGGGAGAGTA GCAGTGCCTT GGACCCCAGC TCTCCTCCCC CTTTCTCTCT AAGGATGGCC    60

CAGAAGGAGA ACTCCTACCC CTGGCCCTAC GGCCGACAGA CGGCTCCATC TGGCCTGAGC   120

ACCCTGCCCC AGCGAGTCCT CCGGAAAGAG CCTGTCACCC CATCTGCACT TGTCCTCATG   180

AGCCGCTCCA ATGTCCAGCC CACAGCTGCC CCTGGCCAGA AGGTGATGGA GAATAGCAGT   240

GGGACACCCG ACATCTTAAC GCGGCACTTC ACAATTGATG ACTTTGAGAT TGGGCGTCCT   300

CTGGGCAAAG GCAAGTTTGG AAACGTGTAC TTGGCTCGGG AGAAGAAAAG CCATTTCATC   360

GTGGCGCTCA AGGTCCTCTT CAAGTCCCAG ATAGAGAAGG AGGGCGTGGA GCATCAGCTG   420

CGCAGAGAGA TCGAAATCCA GGCCCACCTG CACCATCCCA ACATCCTGCG TCTCTACAAC   480

TATTTTTATG ACCGGAGGAG GATCTACTTG ATTCTAGAGT ATGCCCCCCG CGGGGAGCTC   540

TACAAGGAGC TGCAGAAGAG CTGCACATTT GACGAGCAGC GAACAGCCAC GATCATGGAG   600

GAGTTGGCAG ATGCTCTAAT GTACTGCCAT GGGAAGAAGG TGATTCACAG AGACATAAAG   660

CCAGAAAATC TGCTCTTAGG GCTCAAGGGA GAGCTGAAGA TTGCTGACTT CGGCTGGTCT   720

GTGCATGCGC CCTCCCTGAG GAGGAAGACA ATGTGTGGCA CCCTGGACTA CCTGCCCCCA   780

GAGATGATTG AGGGGCGCAT GCACAATGAG AAGGTGGATC TGTGGTGCAT GGAGTGCTT    840

TGCTATGAGC TGCTGGTGGG GAACCCACCC TTCGAGAGTG CATCACACAA CGAGACCTAT   900

CGCCGCATCG TCAAGGTGGA CCTAAAGTTC CCCGCTTCTG TGCCCACGGG AGCCCAGGAC   960

CTCATCTCCA AACTGCTCAG GCATAACCCC TCGGAACGGC TGCCCCTGGC CCAGGTCTCA  1020

GCCCACCCTT GGGTCCGGGC CAACTCTCGG AGGGTGCTGC CTCCCTCTGC CCTTCAATCT  1080

GTCGCCTGAT GGTCCCTGTC ATTCACTCGG GTGCGTGTGT TTGTATGTCT GTGTATGTAT  1140

AGGGGAAAGA AGGGATCCCT AACTGTTCCC TTATCTGTTT CTACCTCCT CCTTTGTTTA   1200

ATAAAGGCTG AAGCTTTTTG TAAAAAAACA AAAAAAAAAA AAAA                   1244
```

(2) INFORMATION FOR SEQ ID NO: 2:

(i) SEQUENCE CHARACTERISTICS:
      (A) LENGTH: 2198 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

```
GGGATATCTC AGTGGCGGAC GAGGACGGCG GGGACAAGGG GCGGCTGGTC GGAGTGGCGG      60
ACGTCAAGTC CCCTGTCGGT TCCTCCGTCC CTGAGTGTCC TTGGCGCTGC CTTGTGCCCG     120
CCCAGCGCCT TTGCATCCGC TCCTGGGCAC CGAGGCGCCC TGTAGGATAC TGCTTGTTAC     180
TTATTACAGC TAGAGGCATC ATGGACCGAT CTAAAGAAAA CTGCATTTCA GGACCTGTTA     240
AGGCTACAGC TCCAGTTGGA GGTCCAAAAC GTGTTCTCGT GACTCAGCAA TTTCCTTGTC     300
AGAATCCATT ACCTGTAAAT AGTGGCCAGG CTCAGCGGGT CTTGTGTCCT TCAAATTCTT     360
CCCAGCGCGT TCCTTTGCAA GCACAAAAGC TTGTCTCCAG TCACAAGCCG GTTCAGAATC     420
AGAAGCAGAA GCAATTGCAG GCAACCAGTG TACCTCATCC TGTCTCCAGG CCACTGAATA     480
ACACCCAAAA GAGCAAGCAG CCCCTGCCAT CGGCACCTGA AAATAATCCT GAGGAGGAAC     540
TGGCATCAAA ACAGAAAAAT GAAGAATCAA AAAGAGGCA GTGGGCTTTG GAAGACTTTG      600
AAATTGGTCG CCCTCTGGGT AAAGGAAAGT TTGGTAATGT TTATTTGGCA AGAGAAAAGC     660
AAAGCAAGTT TATTCTGGCT CTTAAAGTGT TATTTAAAGC TCAGCTGGAG AAAGCCGGAG     720
TGGAGCATCA GCTCAGAAGA GAAGTAGAAA TACAGTCCCA CCTTCGGCAT CCTAATATTC     780
TTAGACTGTA TGGTTATTTC CATGATGCTA CCAGAGTCTA CCTAATTCTG GAATATGCAC     840
CACTTGGAAC AGTTTATAGA GAACTTCAGA AACTTTCAAA GTTTGATGAG CAGAGAACTG     900
CTACTTATAT AACAGAATTG GCAAATGCCC TGTCTTACTG TCATTCGAAG AGAGTTATTC     960
ATAGAGACAT TAAGCCAGAG AACTTACTTC TTGGATCAGC TGGAGAGCTT AAAATTGCAG    1020
ATTTTGGGTG GTCAGTACAT GCTCCATCTT CCAGGAGGAC CACTCTCTGT GGCACCCTGG    1080
ACTACCTGCC CCCTGAAATG ATTGAAGGTC GGATGCATGA TGAGAAGGTG GATCTCTGGA    1140
GCCTTGGAGT TCTTTGCTAT GAATTTTTAG TTGGGAAGCC TCCTTTTGAG GCAAACACAT    1200
ACCAAGAGAC CTACAAAAGA ATATCACGGG TTGAATTCAC ATTCCCTGAC TTTGTAACAG    1260
AGGGAGCCAG GGACCTCATT TCAAGACTGT TGAAGCATAA TCCCAGCCAG AGGCCAATGC    1320
TCAGAGAAGT ACTTGAACAC CCCTGGATCA CAGCAAATTC ATCAAAACCA TCAAATTGCC    1380
AAAACAAAGA ATCAGCTAGC AAACAGTCTT AGGAATCGTG CAGGGGGAGA AATCCTTGAG    1440
CCAGGGCTGC CATATAACCT GACAGGAACA TGCTACTGAA GTTTATTTTA CCATTGACTG    1500
CTGCCCTCAA TCTAGAACGC TACACAAGAA ATATTTGTTT TACTCAGCAG GTGTGCCTTA    1560
ACCTCCCTAT TCAGAAAGCT CCACATCAAT AAACATGACA CTCTGAAGTG AAAGTAGCCA    1620
CGAGAATTGT GCTACTTATA CTGGTTCATA ATCTGGAGGC AAGGTTCGAC TGCAGCCGCC    1680
CCGTCAGCCT GTGCTAGGCA TGGTGTCTTC ACAGGAGGCA AATCCAGAGC CTGGCTGTGG    1740
GGAAAGTGAC CACTCTGCCC TGACCCCGAT CAGTTAAGGA GCTGTGCAAT AACCTTCCTA    1800
GTACCTGAGT GAGTGTGTAA CTTATTGGGT TGGCGAAGCC TGGTAAAGCT GTTGGAATGA    1860
GTATGTGATT CTTTTTAAGT ATGAAAATAA AGATATATGT ACAGACTTGT ATTTTTTCTC    1920
TGGTGGCATT CCTTTAGGAA TGCTGTGTGT CTGTCCGGCA CCCCGGTAGG CCTGATTGGG    1980
TTTCTAGTCC TCCTTAACCA CTTATCTCCC ATATGAGAGT GTGAAAAATA GGAACACGTG    2040
CTCTACCTCC ATTTAGGGAT TTGCTTGGGA TACAGAAGAG GCCATGTGTC TCAGAGCTGT    2100
TAAGGGCTTA TTTTTTTAAA ACATTGGAGT CATAGCATGT GTGTAAACTT TAAATATGCA    2160
AATAAATAAG TATCTATGTC AAAAAAAAAA AAAAAAA                             2198
```

(2) INFORMATION FOR SEQ ID NO: 3:

(i) SEQUENCE CHARACTERISTICS:
        (A) LENGTH: 344 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 3:

```
Met Ala Gln Lys Glu Asn Ser Tyr Pro Trp Pro Tyr Gly Arg Gln Thr
 1               5                  10                  15

Ala Pro Ser Gly Leu Ser Thr Leu Pro Gln Arg Val Leu Arg Lys Glu
                20                  25                  30

Pro Val Thr Pro Ser Ala Leu Val Leu Met Ser Arg Ser Asn Val Gln
            35                  40                  45

Pro Thr Ala Ala Pro Gly Gln Lys Val Met Glu Asn Ser Ser Gly Thr
50                  55                  60

Pro Asp Ile Leu Thr Arg His Phe Thr Ile Asp Asp Phe Glu Ile Gly
65                  70                  75                  80

Arg Pro Leu Gly Lys Gly Lys Phe Gly Asn Val Tyr Leu Ala Arg Glu
                85                  90                  95

Lys Lys Ser His Phe Ile Val Ala Leu Lys Val Leu Phe Lys Ser Gln
                100                 105                 110

Ile Glu Lys Glu Gly Val Glu His Gln Leu Arg Arg Glu Ile Glu Ile
            115                 120                 125

Gln Ala His Leu His His Pro Asn Ile Leu Arg Leu Tyr Asn Tyr Phe
130                 135                 140

Tyr Asp Arg Arg Arg Ile Tyr Leu Ile Leu Glu Tyr Ala Pro Arg Gly
145                 150                 155                 160

Glu Leu Tyr Lys Glu Leu Gln Lys Ser Cys Thr Phe Asp Glu Gln Arg
                165                 170                 175

Thr Ala Thr Ile Met Glu Glu Leu Ala Asp Ala Leu Met Tyr Cys His
                180                 185                 190

Gly Lys Lys Val Ile His Arg Asp Ile Lys Pro Glu Asn Leu Leu Leu
            195                 200                 205

Gly Leu Lys Gly Glu Leu Lys Ile Ala Asp Phe Gly Trp Ser Val His
210                 215                 220

Ala Pro Ser Leu Arg Arg Lys Thr Met Cys Gly Thr Leu Asp Tyr Leu
225                 230                 235                 240

Pro Pro Glu Met Ile Glu Gly Arg Met His Asn Glu Lys Val Asp Leu
                245                 250                 255

Trp Cys Ile Gly Val Leu Cys Tyr Glu Leu Leu Val Gly Asn Pro Pro
                260                 265                 270

Phe Glu Ser Ala Ser His Asn Glu Thr Tyr Arg Arg Ile Val Lys Val
            275                 280                 285

Asp Leu Lys Phe Pro Ala Ser Val Pro Thr Gly Ala Gln Asp Leu Ile
290                 295                 300

Ser Lys Leu Leu Arg His Asn Pro Ser Glu Arg Leu Pro Leu Ala Gln
305                 310                 315                 320

Val Ser Ala His Pro Trp Val Arg Ala Asn Ser Arg Arg Val Leu Pro
                325                 330                 335
```

Pro Ser Ala Leu Gln Ser Val Ala
            340

(2) INFORMATION FOR SEQ ID NO: 4:

(i) SEQUENCE CHARACTERISTICS:
        (A) LENGTH:           403 amino acids
        (B) TYPE:             amino acid
        (C) STRANDEDNESS:     single
        (D) TOPOLOGY:         linear (ii) MOLECULE TYPE:       protein (iii) HYPOTHETICAL:       NO (iv) ANTI-SENSE:          NO (xi) SEQUENCE DESCRIPTION: SEQ ID NO: 4:

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
                20                  25                  30

Cys Gln Asn Pro Leu Pro Val Asn Ser Gly Gln Ala Gln Arg Val Leu
            35                  40                  45

Cys Pro Ser Asn Ser Ser Gln Arg Val Pro Leu Gln Ala Gln Lys Leu
        50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
                100                 105                 110

Glu Leu Ala Ser Lys Gln Lys Asn Glu Glu Ser Lys Lys Arg Gln Trp
            115                 120                 125

Ala Leu Glu Asp Phe Glu Ile Gly Arg Pro Leu Gly Lys Gly Lys Phe
        130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

```
        Glu Phe Leu Val Gly Lys Pro Pro Phe Glu Ala Asn Thr Tyr Gln Glu
                    325                 330                 335

Thr Tyr Lys Arg Ile Ser Arg Val Glu Phe Thr Phe Pro Asp Phe Val
                    340                 345                 350

Thr Glu Gly Ala Arg Asp Leu Ile Ser Arg Leu Leu Lys His Asn Pro
                    355                 360                 365

Ser Gln Arg Pro Met Leu Arg Glu Val Leu Glu His Pro Trp Ile Thr
                    370                 375                 380

Ala Asn Ser Ser Lys Pro Ser Asn Cys Gln Asn Lys Glu Ser Ala Ser
                    385                 390                 395                 400

Lys Gln Ser (2) INFORMATION FOR SEQ ID NO: 5:

(i) SEQUENCE CHARACTERISTICS:
            (A) LENGTH:          11 amino acids
            (B) TYPE:            amino acid
            (C) STRANDEDNESS:    single
            (D) TOPOLOGY:        linear (ii) MOLECULE TYPE:      Peptide (xi) SEQUENCE DESCRIPTION: SEQ ID NO: 5:

Glu Asn Ser Tyr Pro Trp Pro Tyr Gly Arg Gln
1               5                   10

(2) INFORMATION FOR SEQ ID NO: 6:

(i) SEQUENCE CHARACTERISTICS:
            (A) LENGTH:          5 amino acids
            (B) TYPE:            amino acid
            (C) STRANDEDNESS:    single
            (D) TOPOLOGY:        linear (ii) MOLECULE TYPE:      Peptide (xi) SEQUENCE DESCRIPTION: SEQ ID NO: 6:

Cys Ile Ser Gly Pro
1               5

(2) INFORMATION FOR SEQ ID NO: 7:

(i) SEQUENCE CHARACTERISTICS:
            (A) LENGTH:          4 amino acids
            (B) TYPE:            amino acid
            (C) STRANDEDNESS:    single
            (D) TOPOLOGY:        linear (ii) MOLECULE TYPE:      Peptide (xi) SEQUENCE DESCRIPTION: SEQ ID NO: 7:

Gln Phe Pro Gln
1

(2) INFORMATION FOR SEQ ID NO: 8:

(i) SEQUENCE CHARACTERISTICS:
            (A) LENGTH:          5 amino acids
            (B) TYPE:            amino acid
            (C) STRANDEDNESS:    single
            (D) TOPOLOGY:        linear (ii) MOLECULE TYPE:      Peptide (xi) SEQUENCE DESCRIPTION: SEQ ID NO: 8:

Val Asn Ser Gly Gln
1               5
```

(2) INFORMATION FOR SEQ ID NO: 9:

(i) SEQUENCE CHARACTERISTICS:
        (A) LENGTH:          11 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 9:

Arg Lys Glu Pro Val Thr Pro Ser Ala Leu Val
1           5                  10

(2) INFORMATION FOR SEQ ID NO: 10:

(i) SEQUENCE CHARACTERISTICS:
        (A) LENGTH:          13 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 10:

Leu Met Ser Arg Ser Asn Val Gln Pro Thr Ala Ala Pro
1           5                  10

(2) INFORMATION FOR SEQ ID NO: 11:

(i) SEQUENCE CHARACTERISTICS:
        (A) LENGTH:          16 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 11:

Val Gln Asn Gln Lys Gln Lys Gln Leu Gln Ala Thr Ser Val Pro His
1           5                  10              15

(2) INFORMATION FOR SEQ ID NO: 12:

(i) SEQUENCE CHARACTERISTICS:
        (A) LENGTH:          11 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 12:

Pro Val Ser Arg Pro Leu Asn Asn Thr Gln Lys
1           5                  10

(2) INFORMATION FOR SEQ ID NO: 13:

(i) SEQUENCE CHARACTERISTICS:
        (A) LENGTH:          10 amino acids
        (B) TYPE:            amino acid
        (C) STRANDEDNESS:    single
        (D) TOPOLOGY:        linear (ii) MOLECULE TYPE:       Peptide (xi) SEQUENCE DESCRIPTION: SEQ ID NO: 13:

Val Met Glu Asn Ser Ser Gly Thr Pro Asp
1           5                  10

```
(2) INFORMATION FOR SEQ ID NO: 14:

(i) SEQUENCE CHARACTERISTICS:
        (A) LENGTH:           9 amino acids
        (B) TYPE:             amino acid
        (C) STRANDEDNESS:     single
        (D) TOPOLOGY:         linear (ii) MOLECULE TYPE:       Peptide (xi) SEQUENCE DESCRIPTION: SEQ ID NO: 14:

Ile Leu Thr Arg His Phe Thr Ile Asp
 1               5

(2) INFORMATION FOR SEQ ID NO: 15:

(i) SEQUENCE CHARACTERISTICS:
        (A) LENGTH:           22 amino acids
        (B) TYPE:             amino acid
        (C) STRANDEDNESS:     single
        (D) TOPOLOGY:         linear (ii) MOLECULE TYPE:       Peptide (xi) SEQUENCE DESCRIPTION: SEQ ID NO: 15:

Ser Lys Gln Pro Leu Pro Ser Ala Pro Glu Asn Asn Pro Glu Glu Gln
 1               5                  10                  15

Leu Ala Ser Lys Gln Lys
            20

(2) INFORMATION FOR SEQ ID NO: 16:

(i) SEQUENCE CHARACTERISTICS:
        (A) LENGTH:           23 base pairs
        (B) TYPE:             nucleic acid
        (C) STRANDEDNESS:     single
        (D) TOPOLOGY:         linear (ix) FEATURE:
        (D) OTHER INFORMATION:   The letter "R" stands for A or G.
            The letter "Y" stands for C or T.
            The letter "N" stands for A, C, G or T.

(xi) SEQUENCE DESCRIPTION: SEQ ID NO: 16:

GARTTYGGNG ARGTNTTYYT NGC                                          23

(2) INFORMATION FOR SEQ ID NO: 17:

(i) SEQUENCE CHARACTERISTICS:
        (A) LENGTH:           23 base pairs
        (B) TYPE:             nucleic acid
        (C) STRANDEDNESS:     single
        (D) TOPOLOGY:         linear (ix) FEATURE:
        (D) OTHER INFORMATION:   The letter "N" stands for A, C, G or
            T. The letter "R" stands for A or G.

(xi) SEQUENCE DESCRIPTION: SEQ ID NO: 17:

AGNACNCCRA ANGCCCACAC RTC                                          23

(2) INFORMATION FOR SEQ ID NO: 18:

(i) SEQUENCE CHARACTERISTICS:
        (A) LENGTH:           8 amino acids
        (B) TYPE:             amino acid
        (C) STRANDEDNESS:     single
        (D) TOPOLOGY:         linear
```

```
            (ii) MOLECULE TYPE:         Peptide (xi) SEQUENCE DESCRIPTION: SEQ ID NO: 18:

Glu Phe Gly Glu Val Phe Leu Ala
  1               5

(2) INFORMATION FOR SEQ ID NO: 19:

(i) SEQUENCE CHARACTERISTICS:
            (A) LENGTH:                25 base pairs
            (B) TYPE:                  nucleic acid
            (C) STRANDEDNESS:          single
            (D) TOPOLOGY:              linear (xi) SEQUENCE DESCRIPTION: SEQ ID NO: 19:

TTTGGCTCGG GAGAAGAAAA GCCAT                                              25

(2) INFORMATION FOR SEQ ID NO: 20:

(i) SEQUENCE CHARACTERISTICS:
            (A) LENGTH:                24 base pairs
            (B) TYPE:                  nucleic acid
            (C) STRANDEDNESS:          single
            (D) TOPOLOGY:              linear (xi) SEQUENCE DESCRIPTION: SEQ ID NO: 20:

CAATCATCTC TGGGGGCAGG TAGT                                               24

(2) INFORMATION FOR SEQ ID NO: 21:

(i) SEQUENCE CHARACTERISTICS:
            (A) LENGTH:                10 amino acids
            (B) TYPE:                  amino acid
            (C) STRANDEDNESS:          single
            (D) TOPOLOGY:              linear (ii) MOLECULE TYPE:            Peptide (xi) SEQUENCE DESCRIPTION: SEQ ID NO: 21:

Tyr Pro Tyr Asp Val Pro Asp Tyr Ala Ser
  1               5                  10

(2) INFORMATION FOR SEQ ID NO: 22:

(i) SEQUENCE CHARACTERISTICS:
            (A) LENGTH:                14 amino acids
            (B) TYPE:                  amino acid
            (C) STRANDEDNESS:          single
            (D) TOPOLOGY:              linear (ii) MOLECULE TYPE:            Peptide (xi) SEQUENCE DESCRIPTION: SEQ ID NO: 22:

Ser Ala Pro Glu Asn Asn Pro Glu Glu Gln Leu Ala Ser Lys
  1               5                  10

(2) INFORMATION FOR SEQ ID NO: 23:

(i) SEQUENCE CHARACTERISTICS:
            (A) LENGTH:                13 amino acids
            (B) TYPE:                  amino acid
            (C) STRANDEDNESS:          single
            (D) TOPOLOGY:              linear (ii) MOLECULE TYPE:            Peptide (xi) SEQUENCE DESCRIPTION: SEQ ID NO: 23:

Arg Pro Leu Asn Asn Thr Gln Lys Ser Lys Gln Pro Leu
  1               5                  10
```

(2) INFORMATION FOR SEQ ID NO: 24:

(i) SEQUENCE CHARACTERISTICS:
        (A) LENGTH:           13 amino acids
        (B) TYPE:             amino acid
        (C) STRANDEDNESS:    single
        (D) TOPOLOGY:        linear (ii) MOLECULE TYPE:       Peptide (xi) SEQUENCE DESCRIPTION: SEQ ID NO: 24:

Met Ala Gln Lys Glu Asn Ser Tyr Pro Trp Pro Tyr Gly
1             5                   10

(2) INFORMATION FOR SEQ ID NO: 25:

(i) SEQUENCE CHARACTERISTICS:
        (A) LENGTH:           13 amino acids
        (B) TYPE:             amino acid
        (C) STRANDEDNESS:    single
        (D) TOPOLOGY:        linear (ii) MOLECULE TYPE:       Peptide (xi) SEQUENCE DESCRIPTION: SEQ ID NO: 25:

Pro Gly Gln Lys Val Met Glu Asn Ser Ser Gly Thr Pro
1             5                   10

(2) INFORMATION FOR SEQ ID NO: 26:

(i) SEQUENCE CHARACTERISTICS:
        (A) LENGTH:           8 amino acids
        (B) TYPE:             amino acid
        (C) STRANDEDNESS:    single
        (D) TOPOLOGY:        linear (ii) MOLECULE TYPE:       Peptide (ix) FEATURE:
        (D) OTHER INFORMATION:   "Xaa" in positions 2, 4, 5 and 7
            stands for an unidentified amino acid.

(xi) SEQUENCE DESCRIPTION: SEQ ID NO: 26:

Gly Xaa Gly Xaa Xaa Gly Xaa Val
1             5

(2) INFORMATION FOR SEQ ID NO: 27:

(i) SEQUENCE CHARACTERISTICS:
        (A) LENGTH:           9 amino acids
        (B) TYPE:             amino acid
        (C) STRANDEDNESS:    single
        (D) TOPOLOGY:        linear (ii) MOLECULE TYPE:       Peptide (xi) SEQUENCE DESCRIPTION: SEQ ID NO: 27:

Asp Val Trp Ser Tyr Phe Gly Ile Val
1             5

(2) INFORMATION FOR SEQ ID NO: 28:

(i) SEQUENCE CHARACTERISTICS:
        (A) LENGTH:           9 amino acids
        (B) TYPE:             amino acid
        (C) STRANDEDNESS:    single
        (D) TOPOLOGY:        linear (ii) MOLECULE TYPE:       Peptide

```
            (ix) FEATURE:
                  (D) OTHER INFORMATION:   "Xaa" in positions 2 and 6 stands
                        for an unidentified amino acid.

(xi) SEQUENCE DESCRIPTION: SEQ ID NO:  28:

Asp Xaa Trp Ala Ser Xaa Gly Ile Val
      1                   5

(2) INFORMATION FOR SEQ ID NO:  29:

(i) SEQUENCE CHARACTERISTICS:
                  (A) LENGTH:              8 amino acids
                  (B) TYPE:                amino acid
                  (C) STRANDEDNESS:        single
                  (D) TOPOLOGY:            linear (ii) MOLECULE TYPE:            Peptide (ix) FEATURE:
                  (D) OTHER INFORMATION:   "Xaa" in position 4 represents
                        either Asp or Ser.

(xi) SEQUENCE DESCRIPTION: SEQ ID NO:  29:

Asp Val Trp Xaa Phe Gly Val Leu
      1                   5
```

DIAGNOSIS AND TREATMENT OF AUR-1 AND/OR AUR-2 RELATED DISORDERS

RELATED APPLICATIONS

This application relates to U.S. patent application Ser. No. 60/008,809 filed Dec. 18, 1995, now abandoned, and U.S. patent application Ser. No. 60/023,943, filed Aug. 14, 1996, now abandoned, all of which are incorporated herein by reference in their entirety, including any drawings.

FIELD OF THE INVENTION

The present invention relates to the novel protein termed AURORA ONE and AURORA TWO ("AUR-1 and AUR-2"), nucleotide sequences encoding AUR-1 and/or AUR-2, as well as various products and methods useful for the diagnosis and treatment of various AUR-1 and/or AUR-2 related diseases and conditions.

BACKGROUND OF THE INVENTION

The following description of the background of the invention is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function.

The best characterized protein kinases in eukaryotes phosphorylate proteins on the alcohol moiety of serine, threonine and tyrosine residues. These kinases largely fall into two groups, those specific for phosphorylating serines and threonines, and those specific for phosphorylating tyrosines. Some kinases, referred to as "dual specificity" kinases, are able to phosphorylate on tyrosine as well as serine/threonine residues.

Protein kinases can also be characterized by their location within the cell. Some kinases are transmembrane receptor-type proteins capable of directly altering their catalytic activity in response to the external environment such as the binding of a ligand. Others are non-receptor-type proteins lacking any transmembrane domain. They can be found in a variety of cellular compartments from the inner surface of the cell membrane to the nucleus.

Many kinases are involved in regulatory cascades wherein their substrates may include other kinases whose activities are regulated by their phosphorylation state. Ultimately the activity of some downstream effector is modulated by phosphorylation resulting from activation of such a pathway.

The serine/threonine kinase family includes members found at all steps of various signaling cascades, including those involved in controlling cell growth, migration, differentiation and secretion of hormones, phosphorylation of transcription factors resulting in altered gene expression, muscle contraction, glucose metabolism, control of cellular protein synthesis, and regulation of the cell cycle.

SUMMARY OF THE INVENTION

The present invention relates to AUR-1 and/or AUR-2 polypeptides, nucleic acids encoding such polypeptides, cells containing such nucleic acids, antibodies to such polypeptides, assays utilizing such polypeptides, and methods relating to all of the foregoing. The present invention is based upon the isolation and characterization of new proteins which we have designated AUR-1 and/or AUR-2. The polypeptides and nucleic acids may be produced using well known and standard synthesis techniques when given the sequences presented herein. AUR-1 and AUR-2 are related serine/threonine kinases with short N-terminal extensions. The Drosophila and yeast homologs appear to be involved in mitotic regulation. The human proteins appear to be involved in cancer and/or other signal transduction disorders. AUR1 RNA is broadly expressed in rapidly dividing cells, derived from both normal and tumor tissues. AUR2 RNA however, is expressed in a more restricted pattern being low or absent in most normal tissues, and abundant in only a subset of tumor-derived cell lines, particularly those of colorectal origin. Both Aurora1 and Aurora2 show intermediate expression in fetal liver, adult testis, and thymus, suggestive of a normal role for these proteins in meiotic division. Both AUR1 and AUR2 appear to regulate nuclear division, with disruption of their signaling resulting in polyploid cells. This phenotype is likely due to chromosomal missegregation, as seen with their yeast homologue IPL1. Since polyploidy is a hallmark of tumor cells and in cells defective in the p53 tumor suppressor, we are testing the role AUR1 and AUR2 in cellular transformation.

Primary sequence analysis of the human genes reveals that they contain a highly conserved C-terminal protein kinase domain and a weakly conserved N-terminal domain of 74 to 130 amino acids that may play a regulatory role or function as a substrate binding motif. The human genes also contain a cAMP/PKA phosphorylation site R/KR/KXS/T in the activation loop of the kinase domain, which suggests a regulatory pathway similar to the cell cycle regulated CDC2/CDK-related proteins.

Southern analysis with probes derived from the unique N-terminal regions of AUR1 and AUR2 indicate that they exist as a single copy genes in human cells. However, under low stringency conditions, we were able to detect 1.3 kb and 3.2 kb SacI fragments which weakly hybridize to the AUR1 probe. Cloning and sequence analysis reveals this region to encode an intronless AUR1-related pseudogene (termed AUR3), with multiple frame shifts. Furthermore, immediately upstream of the AUR3 pseudogene is a region with complex inverted repeats predicted to form a very stable hairpin loop. AUR3 DNA sequence is homologous to AUR1 beginning from the first nucleotide of the AUR1 cDNA. Immediately upstream of this site, is the predicted hairpin loop of AUR3. We are currently characterizing AUR1 genomic clones to determine if the homology to AUR3 continues upstream from this nucleotide, and whether the AUR1 cDNA includes or preceded by a similar hairpin loop.

The utility of the present invention includes the ability to screen for inhibitors of cell growth and to develop small molecule therapeutics for treating cancers.

Thus, a first aspect the invention features an isolated, enriched, or purified nucleic acid encoding a AUR-1 and/or AUR-2 polypeptide.

By "AUR-1 and/or AUR-2 polypeptide" is meant an amino acid sequence substantially similar to the sequence shown in SEQ ID NO:3 (AUR1) or SEQ ID NO:4 (AUR-2), or fragments thereof. A sequence that is substantially similar will preferably have at least 90% identity (more preferably at least 95% and most preferably 99–100%) to the sequence of SEQ ID NO:3 or SEQ ID NO:4.

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity.

By "isolated" in reference to nucleic acid is meant a polymer of 6 (preferably 21, more preferably 39, most preferably 75) or more nucleotides conjugated to each other, including DNA or RNA that is isolated from a natural source or that is synthesized. In certain embodiments of the invention longer nucleic acids are preferred, for example those of 300, 600, 900 or more nucleotides and/or those having at least 50%, 60%, 75%, 90%, 95% or 99% identity to the full length sequence shown in SEQ ID NO:1 or SEQ ID NO:2. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it and thus is meant to distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two.

However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "a AUR-1 and/or AUR-2 polypeptide" is meant 25 (preferably 30, more preferably 35, most preferably 40) or more contiguous amino acids set forth in the full length amino acid sequence of SEQ ID NO:3 or SEQ ID NO:4, or a functional derivative thereof as described herein. In certain aspects, polypeptides of 100, 200, 300 or more amino acids are preferred. The AUR-1 and/or AUR-2 polypeptide can be encoded by a full-length nucleic acid sequence or any portion of the full-length nucleic acid sequence, so long as a functional activity of the polypeptide is retained.

In preferred embodiments the isolated nucleic acid comprises, consists essentially of, or consists of a nucleic acid sequence set forth in the full length amino acid sequence of SEQ ID NO:3 or SEQ ID NO:4, a functional derivative thereof, or encodes at least 25, 30, 35, 40, 50, 100, 200, or 300 contiguous amino acids thereof; the AUR-1 and/or AUR-2 polypeptide comprises, consists essentially of, or consists of at least 25, 30, 35, or 40 contiguous amino acids of a AUR-1 and/or AUR-2 polypeptide. The nucleic acid may be isolated from a natural source by cDNA cloning or subtractive hybridization; the natural source may be mammalian (human) blood, semen, or tissue and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions. Examples of amino acid sequences of the present invention include the following amino acid sequences (the isolated, purified or enriched nucleic acids encoding them are also within the scope of the present invention):

ENSYPWPYGRQ (SEQ ID NO:5)
CISGP (SEQ ID NO:6)
QFPO (SEQ ID NO:7)
VNSGQ (SEQ ID NO:8)
RKEPVTPSA-LV (SEQ ID NO:9)
LMSRSNVQPTAAP (SEQ ID NO:10)
VQNQKQKQLQATSVPH (SEQ ID NO:11)
PVSRPLNNTQK (SEQ ID NO:12)
VMENSSGTPD (SEQ ID NO:13)
ILTRHFTID (SEQ ID NO:14)
SKQPLPSAPENNPEEQLASKQK (SEQ ID NO:15)

By "conserved nucleic acid regions", are meant regions present on two or more nucleic acids encoding a AUR-1 and/or AUR-2 polypeptide, to which a particular nucleic acid sequence can hybridize under lower stringency conditions. Examples of lower stringency conditions suitable for screening for nucleic acid encoding AUR-1 and/or AUR-2 polypeptides are provided in Abe, et al. *J. Biol. Chem.*, 19:13361 (1992) (hereby incorporated by reference herein in its entirety, including any drawings). Preferably, conserved regions differ by no more than 5 out of 20 nucleotides.

By "unique nucleic acid region" is meant a sequence present in a full length nucleic acid coding for a AUR-1 and/or AUR-2 polypeptide that is not present in a sequence coding for any other naturally occurring polypeptide. Such regions preferably comprise 30 or 45 contiguous nucleotides present in the full length nucleic acid encoding a AUR-1 and/or AUR-2 polypeptide. In particular, a unique nucleic acid region is preferably of mammalian origin.

The invention also features a nucleic acid probe for the detection of a AUR-1 and/or AUR-2 polypeptide or nucleic acid encoding a AUR-1 and/or AUR-2 polypeptide in a sample. The nucleic acid probe contains nucleic acid that will hybridize to a sequence set forth in SEQ ID NO:1 or SEQ ID NO:2 or a functional derivative thereof.

In preferred embodiments the nucleic acid probe hybridizes to nucleic acid encoding at least 12, 75, 90, 105, 120, 150, 200, 250, 300 or 350 contiguous amino acids of the full-length sequence set forth in SEQ ID NO:1 or SEQ ID NO:2 or a functional derivative thereof. Various low or high stringency hybridization conditions may be used depending upon the specificity and selectivity desired. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of AUR-1 and/or AUR-2 RNA in a sample by contacting the sample with a nucleic acid probe under conditions such that hybridization occurs and detecting the presence or amount of the probe bound to AUR-1 and/or AUR-2 RNA. The nucleic acid duplex formed between the probe and a nucleic acid sequence coding for a AUR-1 and/or AUR-2 polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in SEQ ID NO:1 or SEQ ID NO:2 or a functional derivative thereof and a vector or a promoter effective to initiate transcription in a host cell. The recombinant nucleic acid can alternatively contain a transcriptional initiation region functional in a cell, a sequence complimentary to an RNA sequence encoding a AUR-1 and/or AUR-2 polypeptide and a transcriptional termination region functional in a cell.

In another aspect the invention features an isolated, enriched, or purified AUR-1 and/or AUR-2 polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. In certain aspects longer polypeptides are preferred, such as those with 402, 407, 413, or 425 contiguous amino acids set forth in SEQ ID NO:3 or SEQ ID NO:4. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19.

The term is meant to cover only those situations in which man has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments the AUR-1 and/or AUR-2 polypeptide contains at least 25, 30, 35, 40, 50, 100, 150, 200, 250, 300, or 350 contiguous amino acids of the full-length sequence set forth in SEQ ID NO:3 or SEQ ID NO:4, or a functional derivative thereof.

In yet another aspect the invention features an antibody (e.g., a monoclonal or polyclonal antibody) having specific binding affinity to a AUR-1 and/or AUR-2 polypeptide. The antibody contains a sequence of amino acids that is able to specifically bind to a AUR-1 and/or AUR-2 polypeptide. By "specific binding affinity" is meant that the antibody binds to AUR-1 and/or AUR-2 polypeptides with greater affinity than it binds to other polypeptides under specified conditions.

Antibodies having specific binding affinity to a AUR-1 and/or AUR-2 polypeptide may be used in methods for detecting the presence and/or amount of a AUR-1 and/or AUR-2 polypeptide in a sample by contacting the sample with the antibody under conditions such that an immunocomplex forms and detecting the presence and/or amount of the antibody conjugated to the AUR-1 and/or AUR-2 polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a AUR-1 and/or AUR-2 polypeptide. By "hybridoma" is meant an immortalized cell line which is capable of secreting an antibody, for example a AUR-1 and/or AUR-2 antibody. In preferred embodiments the AUR-1 and/or AUR-2 antibody comprises a sequence of amino acids that is able to specifically bind a AUR-1 and/or AUR-2 polypeptide.

In another aspect, the invention describes a polypeptide comprising a recombinant AUR-1 and/or AUR-2 polypeptide or a unique fragment thereof. By "unique fragment," is meant an amino acid sequence present in a full-length AUR-1 and/or AUR-2 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant AUR-1 and/or AUR-2 polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a AUR-1 and/or AUR-2 polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the AUR-1 and/or AUR-2 polypeptide.

In another aspect, the invention features a AUR-1 and/or AUR-2 polypeptide binding agent able to bind to a AUR-1 and/or AUR-2 polypeptide. The binding agent is preferably a purified antibody which recognizes an epitope present on a AUR-1 and/or AUR-2 polypeptide. Other binding agents include molecules which bind to the AUR-1 and/or AUR-2 polypeptide and analogous molecules which bind to a AUR-1 and/or AUR-2 polypeptide. Such binding agents may be identified by using assays that measure AUR-1 and/or AUR-2 binding partner activity, such as those that measure PDGFR activity.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

The invention features a method for screening for human cells containing a AUR-1 and/or AUR-2 polypeptide or an equivalent sequence. The method involves identifying the novel polypeptide in human cells using techniques that are routine and standard in the art, such as those described herein for identifying AUR-1 and/or AUR-2 (e.g., cloning, Southern or Northern blot analysis, in situ hybridization, PCR amplification, etc.).

The invention also features methods of screening human cells for binding partners of AUR-1 and/or AUR-2 polypeptides and screening other organisms for AUR-1 and/or AUR-2 or the corresponding binding partner. The present invention also features the purified, isolated or enriched versions of the peptides identified by the methods described above.

In another aspect, the invention provides an assay to identify agents capable of interfering with the interaction between AUR-1 and/or AUR-2 and a AUR-1 and/or AUR-2 binding partner. Such assays may be performed in vitro or in vivo and are described in detail herein or can be obtained by modifying existing assays, such as the growth assay described in Ser. No. 08/487,088, filed Jun. 7, 1995, now abandoned, (incorporated herein by reference including any drawings) or the assays described in Ser. No. 60/005,167, filed Oct. 13, 1995 (incorporated herein by reference including any drawings). Another assay which could be modified to use the genes of the present invention are described in International Application No. WO 94/23039, published Oct. 13, 1994. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase. Fields and Song, U.S. Pat. No. 5,283,173, issued Feb. 1, 1994 and is incorporated be reference herein.

One means by which inhibitors of Aurora activity may be defined is a screening system using a temperature-sensitive yeast mutant as described by Chan and Botstein (Genetics 135:677–691, 1993); see also Francisco et al., Mol. Cell. Bio. 14(7):4731–4740, 1994) both of which are hereby incorporated herein by reference in their entirety including any drawings. Briefly, yeast strain CCY72-3D-1 (ipl 1-2), which expresses a temperature sensitive form of the yeast homologue of Aurora (ipl1) while viable at 26° C. is incapable of growth at 37° C. Transfection of this strain with an expression plasmid containing a hybrid Aurora gene consisting of the N-terminal portion of ip11, containing the putative substrate interaction domain(s)), and the C-terminal portion of Auroras 1 or 2, containing the catalytic domain, overcomes this sensitivity to growth temperature. The Aurora-expressing yeast strain is then grown at 37° C. in the presence of a test substance. No growth will be evident in the presence of substances that inhibit Aurora catalytic function. Potential inhibitors include small molecular weight chemicals and/or natural products isolation from diverse organisms such as fungi, marine organisms, plants, etc.

The summary of the invention described above is non-limiting and other features and advantages of the invention will be apparent from the following description of the preferred embodiments, and from the claims.

DESCRIPTION OF THE PREFERRED EMBODIMENTS

The present invention relates to AUR-1 and/or AUR-2 polypeptides, nucleic acids encoding such polypeptides, cells, tissues and animals containing such nucleic acids, antibodies to such polypeptides, assays utilizing such polypeptides, and methods relating to all of the foregoing.

I. Nucleic Acid Encoding AUR-1 and/or AUR-2 Polypeptides.

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the AUR-1 and/or AUR-2 gene could be synthesized to give a nucleic acid sequence significantly different from that shown in SEQ ID NO:1 or SEQ ID NO:2. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or SEQ ID NO:2 or a derivative thereof. Any nucleotide or polynucleotide may be used in this regard, provided that its addition, deletion or substitution does not alter the amino acid sequence of SEQ ID NO:3 or SEQ ID NO:4 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the AUR-1 and/or AUR-2 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

II. A Nucleic Acid Probe for the Detection of AUR-1 and/or AUR-2.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "A Guide to Methods and Applications", edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method And Kit For Detecting AUR-1 and/or AUR-2.

One method of detecting the presence of AUR-1 and/or AUR-2 in a sample comprises (a) contacting said sample with the above-described nucleic acid probe, under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of AUR-1 and/or AUR-2 in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising a AUR-1 and/or AUR-2 Nucleic Acid Molecule and Cells Containing These Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecules. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an AUR-1 and/or AUR-2 gene may be obtained by the above-described methods. This region may be retained for its transcriptional termination regulatory sequences, such as termination and polyadenylation. Thus, by retaining the 3'-region naturally contiguous to the DNA sequence encoding an AUR-1 and/or AUR-2 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an AUR-1 and/or AUR-2 sequence) are said to be operably linked if the nature of the linkage between the two DNA sequences does not (1) result in the introduction of a frame-shift mutation, (2) interfere with the ability of the promoter region sequence to direct the transcription of an AUR-1 and/or AUR-2 gene sequence, or (3) interfere with the ability of an AUR-1 and/or AUR-2 gene sequence to be transcribed by the promoter region sequence. Thus, a promoter region would be operably linked to a DNA sequence if the promoter were capable of effecting transcription of that DNA sequence. Thus, to express an AUR-1 and/or AUR-2 gene, transcriptional and translational signals recognized by an appropriate host are necessary.

The present invention encompasses the expression of the AUR-1 and/or AUR-2 gene (or a functional derivative thereof) in either prokaryotic or eukaryotic cells. Prokaryotic hosts are, generally, very efficient and convenient for the production of recombinant proteins and are, therefore, one type of preferred expression system for the AUR-1 and/or AUR-2 gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include ygt10, ygt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express AUR-1 and/or AUR-2 (or a functional derivative thereof) in a prokaryotic cell, it is necessary to operably link the AUR-1 and/or AUR-2 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, λacZ, λacI, and gal promoters of *E. coli*, the α-amylase (Ulmanen et at., *J. Bacteriol.* 162:176–182(1985)) and the ζ-28-specific promoters of *B. subtilis* (Gilman et al., Gene sequence 32:11–20(1984)), the promoters of the bacteriophages of Bacillus (Gryczan, In: The Molecular Biology of the Bacilli, Academic Press, Inc., N.Y. (1982)), and Streptomyces promoters (Ward et at., *Mol. Gen. Genet.* 203:468–478 (1986)). Prokaryotic promoters are reviewed by Glick (*J. Ind. Microbiot.* 1:277–282(1987)); Cenatiempo (*Biochimie* 68:505–516(1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404(1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the AUR-1 and/or AUR-2 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459(1988). Alternatively, baculovirus vectors can be engineered to express large amounts of AUR-1 and/or AUR-2 in insects cells (Jasny, *Science* 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of AUR-1 and/or AUR-2.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of AUR-1 and/or AUR-2 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288(1982)); the TK promoter of Herpes virus (McKnight, *Cell* 31:355–365 (1982)); the SV40 early promoter (Benoist et al., *Nature* (London) 290:304–310(1981)); the yeast gal4 gene sequence promoter (Johnston et al., *Proc. Natl. Acad. Sci.* (*USA*) 79:6971–6975 (1982); Silver et al., *Proc. Natl. Acad. Sci.* (*USA*) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes AUR-1 and/or AUR-2 (or a functional derivative thereof) does not contain any intervening codons which are capable of encoding a methionine (i.e., AUG). The presence of such codons results either in a formation of a fusion protein (if the AUG codon is in the same reading frame as the AUR-1 and/or AUR-2 coding sequence) or a frame-shift mutation (if the AUG codon is not in the same reading frame as the AUR-1 and/or AUR-2 coding sequence).

A AUR-1 and/or AUR-2 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, N.Y. (1982), pp. 307–329). Suitable Streptomyces plasmids include p1J101 (Kendall et al., *J. Bacteriol.* 169:4177–4183 (1987)), and streptomyces bacteriophages such as φC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742(1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274(1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204 (1982); Bollon et at., *J. Ctin. Hematol. Oncol.* 10:39–48 (1980); Maniatis, In: Cell Biology: A Comprehensive Treatise, Vol. 3, Gene Sequence Expression, Academic Press, N.Y., pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of AUR-1 and/or AUR-2 or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. Purified AUR-1 and/or AUR-2 Polypeptides

A variety of methodologies known in the art can be utilized to obtain the peptide of the present invention. The peptide may be purified from tissues or cells which naturally produce the peptide. Alternatively, the above-described isolated nucleic acid fragments could be used to express the AUR-1 and/or AUR-2 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

VI. An Antibody Having Binding Affinity To A AUR-1 and/or AUR-2 Polypeptide And A Hybridoma Containing the Antibody.

The present invention relates to an antibody having binding affinity to a AUR-1 and/or AUR-2 polypeptide. The polypeptide may have the amino acid sequence set forth in SEQ ID NO:3 or SEQ ID NO:4, or functional derivative thereof, or at least 9 contiguous amino acids thereof (preferably, at least 20, 30, 35, or 40 contiguous amino acids thereof).

The present invention also relates to an antibody having specific binding affinity to an AUR-1 and/or AUR-2 polypeptide. Such an antibody may be isolated by comparing its binding affinity to a AUR-1 and/or AUR-2 polypeptide with its binding affinity to another polypeptide. Those which bind selectively to AUR-1 and/or AUR-2 would be chosen for use in methods requiring a distinction between AUR-1 and/or AUR-2 and other polypeptides. Such methods could include, but should not be limited to, the analysis of altered AUR-1 and/or AUR-2 expression in tissue containing other polypeptides.

The AUR-1 and/or AUR-2 proteins of the present invention can be used in a variety of procedures and methods, such as for the generation of antibodies, for use in identifying pharmaceutical compositions, and for studying DNA/protein interaction.

The AUR-1 and/or AUR-2 peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., *J. Immunol. Methods* 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, "Monoclonal Antibody Technology: Laboratory Techniques in Biochemistry and Molecular Biology", supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., *J. Histochem. Cytochem.* 18:315 (1970); Bayer et at., *Meth. Enzym.* 62:308 (1979); Engval et al.,*Immunot.* 109:129(1972); Goding,*J. Immunol. Meth.* 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10(1986); Jacoby et al., *Meth. Enzym.* 34, Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, N.Y., pp. 289–307 (1992), and Kaspczak et al., Biochemistry 28:9230–8(1989).

Anti-peptide peptides can be generated by replacing the basic amino acid residues found in the AUR-1 and/or AUR-2 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VII. An Antibody Based Method And Kit For Detecting AUR-1 and/or AUR-2.

The present invention encompasses a method of detecting an AUR-1 and/or AUR-2 polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels of AUR-1 and/or AUR-2 in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is capable with the system utilized.

A kit contains all the necessary reagents to carry out the previously described methods of detection. The kit may comprise: (i) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VIII. Isolation of Compounds Which Interact With AUR-1 and/or AUR-2.

The present invention also relates to a method of detecting a compound capable of binding to a AUR-1 and/or AUR-2 polypeptide comprising incubating the compound with AUR-1 and/or AUR-2 and detecting the presence of the compound bound to AUR-1 and/or AUR-2. The compound may be present within a complex mixture, for example, serum, body fluid, or cell extracts.

The present invention also relates to a method of detecting an agonist or antagonist of AUR-1 and/or AUR-2 activity or AUR-1 and/or AUR-2 binding partner activity comprising incubating cells that produce AUR-1 and/or AUR-2 in the presence of a compound and detecting changes in the level of AUR-1 and/or AUR-2 activity or AUR-1 and/or AUR-2 binding partner activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing AUR-1 and/or AUR-2 associated activity in a mammal comprising administering to said mammal an agonist or antagonist to AUR-1 and/or AUR-2 in an amount sufficient to effect said agonism or antagonism. A method of treating diseases in a mammal with an agonist or antagonist of AUR-1 and/or AUR-2 related activity comprising administering the agonist or antagonist to a mammal in an amount sufficient to agonize or antagonize AUR-1 and/or AUR-2 associated functions is also encompassed in the present application.

IX. Transgenic Animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897–905 (1991). Other procedures for introduction of DNA into tissues of animals are described in U.S. Pat. No., 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

Thus, the invention provides transgenic, nonhuman mammals containing a transgene encoding a AUR-1 and/or AUR-2 polypeptide or a gene effecting the expression of a AUR-1 and/or AUR-2 polypeptide. Such transgenic nonhuman mammals are particularly useful as an in vivo test system for studying the effects of introducing a AUR-1 and/or AUR-2 polypeptide, regulating the expression of a AUR-1 and/or AUR-2 polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human AUR-1 and/or AUR-2 polypeptide. Native expression in an animal may be reduced by providing an amount of antisense RNA or DNA effective to reduce expression of the receptor.

X. Gene Therapy

AUR-1 and/or AUR-2 or its genetic sequences will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926–931, (1993).

In one preferred embodiment, an expression vector containing the AUR-1 and/or AUR-2 coding sequence is inserted into cells, the cells are grown in vitro and then infused in large numbers into patients. In another preferred embodiment, a DNA segment containing a promoter of choice (for example a strong promoter) is transferred into cells containing an endogenous AUR-1 and/or AUR-2 in such a manner that the promoter segment enhances expression of the endogenous AUR-1 and/or AUR-2 gene (for example, the promoter segment is transferred to the cell such that it becomes directly linked to the endogenous AUR-1 and/or AUR-2 gene).

The gene therapy may involve the use of an adenovirus containing AUR-1 and/or AUR-2 cDNA targeted to a tumor, systemic AUR-1 and/or AUR-2 increase by implantation of engineered cells, injection with AUR-1 and/or AUR-2 virus, or injection of naked AUR-1 and/or AUR-2 DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant AUR-1 and/or AUR-2 protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted systems e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi MR, Cell 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52 (1987)); electroporation, wherein cells are exposed to large voltage pulses to introduce holes into the membrane (Chu G. et al., Nucleic Acids Res., 15:1311–26 (1987)); lipofection/liposome fusion, wherein DNA is packaged into lipophilic vesicles which fuse with a target cell (Felgner PL., et al., Proc. Natl. Acad. Sci. USA. 84:7413–7 (1987)); and particle bombardment using DNA bound to small projectiles (Yang N S. et al., Proc. Natl. Acad. Sci. 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel DT et al., Am. J. Respir. Cell. Mol. Biol., 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a AUR-1 and/or AUR-2 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

EXAMPLES

The examples below are non-limiting and are merely representative of various aspects and features of the present invention. The examples below demonstrate the isolation, and characterization of the novel proteins AUR-1 and AUR-2.

Protein kinases are one of the largest families of eukaryotic proteins with several hundred known members. These proteins share a 250–300 amino acid domain that can be subdivided into 12 distinct subdomains that comprise the common catalytic core structure. These conserved protein motifs have recently been exploited using PCR-based cloning strategies leading to a significant expansion of the known kinases. Multiple alignment of the sequences in the catalytic domain of protein kinases and subsequent phylogenetic analysis permits their segregation into a phylogenetic tree. In this manner, related kinases are clustered into distinct branches or subfamilies including: tyrosine kinases, cyclic-nucleotide-dependent kinases, calcium/calmodulin kinases, cyclin-dependent kinases and MAP-kinases, as well as several other less defined subfamilies.

Initially we set out to identify homologues of CCK4, a receptor that represents a distinct family of tyrosine kinases. Multiple alignments suggested CCK4 was most closely related to ROS and the TRK-family of receptor tyrosine kinases. We designed degenerate primers to conserved sequences within kinase subdomains I and IX of these receptors. Subdomain I is at the N-terminus of the kinase domain and contains the consensus motif GXGXXGXV which is involved in anchoring ATP to the catalytic unit of all classes of kinases. Subdomain IX contains a nearly invariant Asp which acts to stabilize the catalytic loop by bonding to residues in subdomain VIB. This invariant Asp and flanking amino acids are often used in PCR-cloning strategies as it distinguishes tyrosine-kinases (DVWSY/FGI/V) from serine/threonine kinases (DXWA/SXGI/V). Based on comparison of all known protein kinases, we designed degenerate oligonucleotide primers to subdomains I and IX that would pick up only CCK4 and its chicken homologue KLG by PCR.

We designed degenerate primers A and DVW based on conserved residues within the kinase domain of CCK4, to use for identification of novel kinases using polymerase chain reaction (PCR). When applied to HEPM cell sscDNA as a template, multiple copies of CCK4 were isolated as well as a novel DNA fragment (43–43) of 567 bp with homology to other kinases. The novel sequence was most similar to Drosophila aurora kinase (GeneBank Accession #X83465)

and the clone was designated human Aurora1. Using this fragment as a probe, we screened RNAs from a number of colon cancer cell lines and a human multiple tissue Northern blot, demonstrating an apparent selectivity in expression of Aurora1 in tumor cells.

The Aurora1 probe was also used to screen a cDNA library constructed from human pancreatic cancer cell line mRNA to isolate overlapping clones spanning the complete open reading frame of Aurora1. Of multiple clones isolated, seven corresponded to human Auroral. Two additional faintly hybridizing clones were also isolated during this screen and sequence analysis revealed they corresponded to a related, yet distinct kinase, which we designated human Aurora2.

Recombinant AURORA1 and AURORA2 expressed in COS cells migrated with apparent Mr of 39,000 and 46,000, consistent with their predicted molecular weights of 39264 and 46730 based on their primary amino acid sequence. This analysis confirms the recombinant protein can be stably produced in mammalian cells. Phosphorylation assays to determine target specificity of these putative kinases are ongoing.

Specific immunoreagents were generated in rabbits against peptide sequence from the N-terminal domains of AUR1 and AUR2 have these reagents to localize expression of endogenous and recombinant Auroras within the cells. Furthermore, these reagents can be used in an effort to identify substrates for the AURORAs in order to better understand their normal biological role.

Dominant negative and constitutively active forms of AUR1 and AUR2 will be useful for delineating biologic consequences of either oblation or overexpression of these putative serine/threonine kinases. Initial studies with altered DNA constructs demonstrates that in just 2 hours following infection of NIH3T3 or BALB/3T3 cells with AUR1 or AUR2 retroviral stocks, cells become multinucleated. This phenotype persisted such that 2 days after infection some cells were found to have as many as 20 nuclei. The multinucleated cells typically had increased cytoplasm and diffuse cell boundaries. Immunostaining with both actin and DAPI, confirmed these nuclei were all contained within a single cell, and that the actin cytoskeleton was apparently normal. Ongoing experiments will address the chromosome content and intactness within the nuclei, the number and location of centrosomes, and the general organization of the microtubule network.

Characterization of the long term consequences of expression of AUR1 or AUR2 normal, constitutively active and dominant negative are underway, and particularly whether they induce or reverse cellular transformation. Stable clones are being isolated that express these recombinant proteins. They will be characterized for growth rate, DNA synthesis, cell-contact inhibition (foci formation), anchorage-independent growth (soft agar assays), and tumorigenicity in nude mice.

What role do the Auroras play in mammalian centrosome replication and segregation? Disruption or deregulation of such functions is known to result in chromosome missegregation, monopolar spindles, and asymetric nuclear division in yeast, drosophila, and amphibians. The homology between human Auroras and the yeast IPL1 and drosophila aurora is striking. We therefore desire to assess if the human auroras are functional equivalents of the yeast IPL1. The yeast IPL1 gene is required for high-fidelity chromosome segregation in *Saccharomyces cerevisiae* (Francisco, L., et al., Mol. Cell. Biol. 14:4731–4740, 1994) and a temperature sensitive mutant has been isolated. We plan to determine if various full length and chimeric versions of the human Auroras can complement this temperature sensitive mutant in yeast. The chimeric constructs containing the N-terminal domain of IPL1 and the kinase domain of the human auroras will permit us to determine if the kinase is functionally equivalent, while avoiding potential regulatory or intracellular localization roles mediated by the less well conserved N-terminal domains. Should the human genes compensate for the IPL1 loss of function, we could then use such a line to screen for small molecule inhibitors of the human aurora kinase.

Example 1

MOLECULAR CLONING

Total RNAs were isolated using the Guanidine Salts/Phenol extraction protocol of Chomczynski and Sacchi (P. Chomczynski and N. Sacchi, Anal. Biochem. 162, 156 (1987) from normal human prostate, duodenum, ovary, liver, pituitary, brain, thymus, and salivary gland, from human HEPM cells (palatal mesenchyme), from primary human Wilm's tumor and ovarian carcinoma, and from human tumor cell lines originating from colon/rectum (HT29, SW480, SW1463, SW1417, SW837, SW948, SW620, SW403, SW1116, T84, HTCl5, LS123, and Caco-2), kidney (CaKi-1, CaKi-2), liver (SK-HEP-1), pancreas (HS766T, ASPC, Capan-1), and breast (MCF7).

These RNAs were used as templates to generate single-stranded cDNAs using the Superscript Preamplification System for First Strand Synthesis kit purchased from GibcoBRL (Life Technologies, U.S.A.; Gerard, GF et al. (1989), FOCUS 11, 66) under conditions recommended by manufacturer. A typical reaction used 10 ug total RNA or 2 ug poly(A)$^+$ RNA with 1.5 ug oligo(dT)$_{12-18}$ in a reaction volume of 60 ul. The product was treated with RNaseH and diluted to 100 ul with H20. For subsequent PCR amplification, 1–4 ul of these sscDNAs were used in each reaction.

Oligonucleotides were synthesized on an Applied Biosystems 394 DNA synthesizer using established phosphoramidite chemistry and were used unpurified after precipitation with ethanol. The degenerate oligonucleotide primers are:
A=5'-GARTTYGGNGARGTNTTYYTNGC-3' (SEQ ID NO:16) (sense) and
DVW=5'-AGNACNCCRAANGCCCACACRTC-3' (SEQ ID NO:17) (antisense).

These primers were derived from the peptide sequences EFGEVFLA (SEQ ID NO:18) (sense strand from kinase subdomain I) and DVW(A/S)FGVL (antisense strand from kinase subdomain IX), respectively. Degenerate nucleotide residue designations are: N=A, C, G, or T; R=A or G; and Y=C or T. Using CCK4 as a template, these primers produce a product of 567 bp.

A PCR reaction was performed using Primers A and DVW applied to the single-stranded sources listed above. The primers were added at a final concentration of 5 uM each to a mixture containing 10 mM Tris-HCl (pH8.3), 50 mM KCl, 1.5 mM MgCl$_2$, 200 uM each deoxynucleoside triphosphate, 0.001% gelatin, and 1.5 U AmpliTaq DNA Polymerase (Perkin-Elmer/Cetus), and 1–4 ul cDNA. Following 3 min denaturation at 95° C., the cycling conditions were 94° C. for 30 s, 37° C. for 1 min, a 2 min ramp to 72° C., and 72° C. for 1 min for the first 3 cycles, followed by 94° C. for 30 s, 50° C. for 1 min, and 72° C. for 1 min 45 s for 35 cycles. PCR fragments migrating at between 500–600 bp were isolated from 2% agaorse gels using GeneClean (Bio101), and T-A cloned into the pCRII vector (Invitrogen Corp. U.S.A.) according to the manufacturer's protocol.

Colonies were selected for mini plasmid DNA-preparations using Qiagen columns and the plasmid DNAs were sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., J. Mol. Biol.215:403–10). A novel clone (#43–43) was isolated by PCR with primers A and DVW on single-stranded cDNA from human embryonic palatal mesenchyme (HEPM or CRL1486) as a template. This clone was subsequently designated as a fragment of human Aurora1.

A lambda ZapII (Stratagene Cloning Systems, La Jolla, Calif.) cDNA library was constructed using mRNA from a pool of pancreatic carcinoma cell lines as a template for first strand cDNA synthesis. Phage were screened on nitrocellulose filters with the random primed $^{32}$P-labeled insert from p43—43 encoding human Aurora1 at $2\times10^6$ cpm/ml in hybridization buffer containing 6×SSC, 1× Denhardt's reagent, 0.1% SDS, with 0.1 mg/ml denatured, fragmented salmon sperm DNA. After overnight hybridization at 65° C., filters were washed in 0.1×SSC, 0.1%SDS at 65° C. Full length cDNA clones were sequenced on both strands using manual sequencing with T7 polymerase and oligonucleotide primers (Tabor and Richardson, 1987, Proc. Natl. Acad. Sci. U.S.A. 84: 4767–71).

Example 2
NORTHERN BLOT ANALYSIS

Northern blots containing 2 ug poly A+RNA per lane from 16 different adult human tissues (spleen, thymus, prostate, testis, ovary, small intestine, colonic mucosa, heart, brain, placenta, lung, liver, skeletal muscle, kidney, pancreas, and peripheral blood leukocytes), four different human fetal tissues (brain, lung, liver, and kidney), and 8 human cancer cell lines (HL60, HeLa, K-562, MOLT-4, Raji, SW480, and G361) on a charge-modified nylon membrane were obtained from Clontech (Palo Alto, Calif.). Additional Northern blots were prepared by running 10 ug total RNA isolated from human tumor cell lines on a denaturing formaldehyde 1.2% agarose gel and transferring to nylon membranes.

Filters were hybridized with random prime [$^{32}$P] dCTP-labeled probes synthesized from either the 527 bp insert from human Aurora1 clone 43—43 or the 1162 bp EcoRI fragment from pSG20, and either the 1 kb EcoRI fragment of human Aurora2 clone 11-1A or the 1257 bp BamHI-Not I fragment from pS621. Hybridization was performed at 60° C. overnight in 6XSSC, 0.1% SDS, 1× Denhardt's solution, 100 mg/ml denatured herring sperm DNA with $1-2\times10^6$ cpm/ml of $^{32}$P-labeled DNA probes. The filters were washed in 0.1×SSC/0.1% SDS, 65° C., and exposed overnight on Kodak XAR-2 film.

A single AUR1 mRNA transcript of approximately 1.4 kb was identified, and was found to be most abundant in the thymus and small intestine with weak signals from testis, ovary, colon, placenta, and spleen. Prostate and peripheral blood lymphocytes were negative. Human fetal liver and kidney were also positive, with a weaker signal in fetal lung and no expression in fetal brain (Table)

A similar analysis of human AUR2 expression showed a more restricted expression profile. A single 2.4 kb AUR2 transcript was detected strongly in the adult testis and thymus, and weakly in heart, placenta, skeletal muscles and in fetal liver and kidney (see Table). As set forth in the Table, the 2.4 kb AUR2 transcript was not detected in other normal tissue sources.

AURORA 1 and AURORA 2 NORTHERN ANALYSIS IN HUMAN NORMAL TISSUE AND CANCER CELLS

| Cell type | Origin | AUR 1 | AUR 2 |
| --- | --- | --- | --- |
| Thymus | Normal tissue | 5 | 4 |
| Fetal liver | Normal tissue | 4 | 2 |
| Fetal kidney | Normal tissue | 4 | 1 |
| Lung | Normal tissue | 3 | 0 |
| Duodenum | Normal tissue | 2 | 1 |
| Colon | Normal tissue | 2 | 0 |
| Fetal lung | Normal tissue | 2 | 0 |
| Ovary | Normal tissue | 2 | 0 |
| Testis | Normal tissue | 2 | 2 |
| Brain | Normal tissue | 0 | 0 |
| Cerebellum | Normal tissue | 0 | 0 |
| Salivary gland | Normal tissue | 0 | 0 |
| Heart | Normal tissue | 0 | 0 |
| Liver | Normal tissue | 0 | 0 |
| Pancreas | Normal tissue | 0 | 0 |
| Kidney | Normal tissue | 0 | 0 |
| Spleen | Normal tissue | 0 | 0 |
| Stomach | Normal tissue | 0 | 0 |
| Uterus | Normal tissue | 0 | 0 |
| Prostate | Normal tissue | 0 | 0 |
| Skeletal muscle | Normal tissue | 0 | 0 |
| Fetal brain | Normal tissue | 0 | 0 |
| PBLs | Normal tissue | 0 | 0 |
| Salivary gland | Normal tissue | 0 | 0 |
| Placenta | Normal tissue | 0 | 0 |
| SF-268 | CNS tumor | 4 | ND |
| CCRF-CEM | Leukemia | 4 | ND |
| K-562 | Leukemia | 4 | ND |
| HCC-2998 | Colon tumor | 4 | ND |
| SW620 | Colon tumor | 4 | 2 |
| KM-12 | Leukemia | 4 | ND |
| MCF7/ADR-RES | Breast tumor | 4 | 2 |
| MDA-N | Breast tumor | 4 | ND |
| BT-549 | Breast tumor | 4 | ND |
| SW480 | Colon tumor | 4 | 4 |
| SW48 | Colon tumor | 4 | ND |
| Calu-3 | Lung tumor | 4 | ND |
| Calu3 | Lung tumor | 4 | 2 |
| T47D | Breast tumor | 4 | 2 |
| A375 | Melanoma | 4 | 0 |
| SF767 | CNS tumor | 4 | 0 |
| SW1417 | Colon tumor | 4 | 4 |
| CaKi2 | Kidney tumor | 4 | 0 |
| CaKi1 | Kidney tumor | 4 | 0 |
| Caco2 | Colon tumor | 4 | 4 |
| SW1417 | Colon tumor | 4 | 0 |
| T98G | CNS tumor | 4 | 0 |
| SF-539 | CNS tumor | 3 | ND |
| SK-MEL-2 | Melanoma | 3 | ND |
| SK-MEL-5 | Melanoma | 3 | ND |
| R-48 | Gastric tumor | 3 | ND |
| RF-1 | Gastric tumor | 3 | ND |
| SW948 | Colon tumor | 3 | ND |
| AGS | Gastric tumor | 3 | ND |
| HFL1 | Normal lung | 3 | ND |
| OVCAR-8 | Ovarian tumor | 2 | ND |
| HT-29 | Colon tumor | 2 | ND |
| MDA-MB-231 | Breast tumor | 2 | ND |
| MDA-MB-435 | Breast tumor | 2 | ND |
| SK-MEL-5 | Melanoma | 2 | ND |
| Kato-3 | Gastric tumor | 2 | ND |
| Colo 205 | Colon tumor | 2 | ND |
| Colo 320DM | Colon tumor | 2 | 2 |
| WiDr | Colon tumor | 2 | ND |
| HT-29 | Colon tumor | 2 | ND |
| SNU-C2B | Colon tumor | 2 | ND |
| HTC15 | Colon tumor | 2 | 2 |
| T84 | Colon tumor | 2 | 0 |
| SW948 | Colon tumor | 2 | 0 |
| Daoy | CNS tumor | 2 | 0 |
| OVCAR3 | Ovary tumor | 2 | 0 |
| HS766T | Pancreas tumor | 2 | 0 |
| SW1116 | Colon tumor | 2 | 0 |

-continued

AURORA 1 and AURORA 2 NORTHERN ANALYSIS IN HUMAN
NORMAL TISSUE AND CANCER CELLS

| Cell type | Origin | AUR 1 | AUR 2 |
|---|---|---|---|
| Wilms tumor | Kidney tumor | 2 | 0 |
| UO-31 | Renal tumor | 0 | ND |

The AUR1 mRNA expression profile in several primary tumors and multiple cell lines of diverse neoplastic origin was determined by Northern analysis and by the semi-quantitative PCR assay using primers from sequences in the AUR1 kinase domain. The results are included in Table. AUR1 transcripts were detected in every tumor line assayed with the highest expression in several human colon cancer cell lines (SW480, Colo320, SW620, SW1417, Caco2, SW12417) and in lung carcinoma (Calu3), breast carcinoma (T47D, MCF7), Melanoma (A375), Kidney carcinoma (CaKi-1, CaKi-2), liver carcinoma (SK-HEP-1), and neural tumors (SF767, T98G). Lesser expression of AUR1 was seen in other colon carcinomas (HTC15, T84, SW948, SW1116, HT29), neural tumors (Daoy), Ovarian carcinoma (Ovcar3, Primary tumor), pancreatic carcinoma (HS766T), and a primary kidney tumor.

The AUR2 expression profile in tumor cell lines was strikingly more restricted than that of AUR1. Strong expression of AUR2 was detected only in colon carcinoma cell lines (Caco2, SW480, SW1417, SW620) whereas weak signals were seen in other colon (HTC15, Colo320), Breast (T47D, MCF7) and lung (Calu3) tumor cell lines. Several other tumor lines had no detectable AUR2 transcripts.

Example 3
Semi-Quantitative PCR Detection of Aurora1

RNA was isolated from a variety of human cell lines, fresh frozen tissues, and primary tumors. Single stranded cDNA was synthesized from 10 mg of each RNA as described above using the Superscript Preamplification System (GibcoBRL). These single strand templates were then used in a 35 cycle PCR reaction with two AURORA1-specific oligonucleotides (3476: 5'-TTTGGCTCGGGAGAAGAAAAGCCAT-3' (SEQ ID NO:19), and 3506: 5'-CAATCATCTCTGGGGGCAGGTAGT-3') (SEQ ID NO:20). Reaction products were electrophoresed on 2% agarose gels, stained with ethidium bromide and photographed on a UV light box. The relative intensity of the ~475-bp AURORA1-specific bands were estimated for each sample.

Example 4
Southern Blot Analysis

Genomic DNA was isolated from a variety of transformed human lines (CaCO2, HTC15, LS147T, SKCO4, SW480, SW403, SW620, SW948, SW1417, SW1116, MCF7, BT474) using standard procedures (Maniatis et al.). Cells were trypsinized, washed with PBS and resuspended at ~$10^8$ cells/ml in Digestion buffer (100 mM NaCl, 10 mM Tris pH8, 25 mM EDTA, pH8, 0.5%SDS, 0.1 mg/ml proteinase K). Cells were lysed by incubation at 50° C. for 12 hours, followed by extraction with phenol/chloroform and precipitated with an equal volume of 7.5M ammonium acetate and 100% EtOH. DNAs were resuspended in TE buffer. Approximately 20 micrograms genomic DNA was digested with HindIII or XhoII at 37° C. for at least 4 hours before fractionation on 1% agarose gels. The DNA fragments were transferred to nitrocellulose membranes by the capillary transfer method (Southern, EM, J Mol Bio 98:503, 1975) and hybridized with human Aurora1 and Aurora2-specifc probes as described for Northern Blot analysis above.

DNAs were restricted with HindIII since both AUR1 and AUR2 cDNAs contain a single site for this restriction enzyme. AUR1 showed a single 4.3 kb band of equal intensity from all sources suggesting it is a single copy, non-rearranged gene in the multiple tumor types assayed. However, under low stringency conditions, we were able to detect 1.3 kb and 3.2 kb SacI fragments which weakly hybridize to the AUR1 probe. Cloning and sequence analysis reveals this region to encode an intronless AUR1-related pseudogene (termed AUR3), with multiple frame shifts. Furthermore, immediately upstream of the AUR3 pseudogene is a region with complex inverted repeats predicted to form a very stable hairpin loop. AUR3 DNA sequence is homologous to AURI beginning from the first nucleotide of the AUR1 cDNA. Immediately upstream of this site, is the predicted hairpin loop of AUR3. We are currently characterizing AUR1 genomic clones to determine if the homology to AUR3 continues upstream from this nucleotide, and whether the AUR1 cDNA includes or be preceded by a similar hairpin loop. AUR2 showed bands at 7.0 kb and 4.3 kb and a faint higher molecular weight band at ~10 kb from all sources. These data suggest AUR2 is also a single copy gene. The multiple bands with seen on blots probed with AUR2 are likely due to the fact that a full length cDNA probe was used.

Example 5
Sequence Analysis of cDNA Clones Encoding Human Aurora1 and Aurora2

The complete sequence of human Aurora1 and Aurora2 was determined from full length clones of each isolated from the human pancreatic carcinoma library, from normal human duodenum, and from the partial human Aurora1 isolated from HEPM cells.

The 1,244 bp human Aurora1 (AUR1_h) nucleotide sequence is shown in SEQ ID NO:1 and contains a single open reading frame encoding a polypeptide of 344 amino acids. The AUR1_h coding region is flanked by a 54 nucleotide 5'-untranslated region and a 132 nucleotide 3'-untranslated region ending with a poly(A) tail.

The 2,198 bp human Aurora2 (AUR2_h) nucleotide sequence is shown in SEQ ID NO:2 and contains a single open reading frame encoding a polypeptide of 403 amino acids. The AUR2_h coding region is flanked by a 200 nucleotide 5'-untranslated region and a 768 nucleotide 3'-untranslated region.

The sequences AUR1 and AUR2 cDNAs were sequenced from both a human pancreatic tumor and normal human duodenum, with no sequence differences excepting some likely polymorphic sites. These ambiguities include:

| cDNA | nucleotide | Comment |
|---|---|---|
| AUR1 | 1174 | one clone has poly A inserted |
|  | 873 | T in all duodenal clones, C in pancreatic tumor |
|  | 469 | T in one clone, C in all others |
|  | 848 | G in one clone, A in all others - changes amino acid E to G |
|  | 1097 | G in one clone, T in 2 others |
|  | 956 | G in one clone, A in 4 others |
|  | 29 | Splice to 103 in 5 clones, no splice (as sown in 5 clones |
| AUR2 | 349 | T in 1 cline, C in multiple others (change amino acid P to L) |

-continued

| cDNA | nucleotide | Comment |
|---|---|---|
| | 369 | A in 3 clones, G in multiple others (change AA V to I) |

The C-terminal portions AUR1 and AUR2 conserve all 12 subdomains characteristic of eukaryotic protein kinases. The AUR1 and AUR2 kinase domains are preceded by a N-terminal domain of 74 and 130 amino acids, respectively. Comparison of the AUR1 and AUR2 nucleotide and deduced amino acid sequences (SEQ ID NO:3 or SEQ ID NO:4) with the available DNA and protein sequence databases indicated that they are unique with the exception of several EST sequences sharing high sequence identity. They do however have striking homology in both the N-terminal and catalytic domains with the drosophila aurora and *Saccharomyces cerevisiae* IPL1 genes. Furthermore two unpublished database entries are likely to be close homologues from *Xenopus laevis* (p46APK—GB accession #Z17206 and p46BPK—GB accession #Z17207).

The N-terminal domains of Auroras from human, frog, Drosophila and yeast share limited sequence identity. The AUR2 has an abundance of glutamates often present in pairs separated by a single residue.

Comparison of the catalytic domains of these protein reveals AUR1 shares 70% amino acid identity with AUR2, 61% with the Drosophila aurora, and 45% with the yeast IPL1 gene. AUR2 kinase shares 60% amino acid identity with the Drosophila protein and 45% identity to yeast IPL1. Both AUR1 and AUR2 share less than 45% homology with all other known mammalian kinases (the closest being cAMP-dependent protein kinase A) suggesting they are homologues of these drosophila and yeast kinases.

AUR1 and AUR2 both contain a cAMP-dependent protein kinase phosphorylation site (THR232 of AUR1 and THR288 of AUR2) that is conserved in the drosophila and yeast homologues and is a known regulatory site in the cylclin-dependent kinase p34cdc2. AUR2 contains an additional PKA-site at SER342. Both proteins also have multiple Casein kinase II (five and six for AUR1 and AUR2) and protein kinase C (four and ten for AUR1 and AUR2) phosphorylation sites. AUR2 also has a single tyrosine phosphorylation consensus site at TYR334 that is also conserved with the Drosophila aurora, but is not present in AUR1 or yeast IPL1.

Intriguingly, natural mutants of the drosophila aurora AUR_dm and yeast IPL1 gene result in asymmetric nuclear division leading to chromosome missegregation, and atypical, monopolar spindles. This phenotype appears to result from a failure of centrosome separation. The associated microtubule architecture appear unaffected. Natural mutants in both drosophila and yeast target amino acid residues that are strictly conserved between the human Auroras, further supporting they may be functional homologues. The corresponding residues in AUR1 that are found in natural mutants of AUR_dm or IPL1 are GLU125, THR232, PRO312, HIS324. All of these mutations are within the catalytic domain, and notably, one represents the conserved PKA-phosphorylation site. An additional mutation in $AUR_{13}$ dm at ASP47 is at a non-conserved residue in the N-terminal domain.

These findings suggest the catalytic activity may indeed play a central role in the biology of centrosome replication or segregation in lower organisms, and suggest that the human Auroras may play a complementary role in mammalian cells.

Example 6
Recombinant Expression of Aurora and Aurora2 Expression Vector Construction Expression constructs were generated by PCR-assisted mutagenesis in which the entire coding domains of Aurora1 and Aurora2 were tagged on their carboxy-terminal ends with the hemophilus influenza hemaglutinin (HA) epitope YPYDVPDYAS (SEQ ID NO:21) (Pati, 1992). These constructs were introduced into two mammalian expression vectors: PLXSN (Miller, A. D. & Rosman, G. J., Biotechniques 7, 980–988, 1989) for the generation of virus producing lines; and pRK5 for transient expression analysis. Inserts were designed to be flanked by unique BamHI and NotI sites and were cloned directly into pLXSN or pRK5 at the 5'-BamHI and 3'-NotI sites.

The BamHI-NotI full length AUR1 and AUR2 constructs were also ligated into pRS316 (Liu, H. et al, Genetics 132:665–673, 1992). This vector contains a galactose-inducible promoter in a centromeric shuttle vector for expression in Saccharomyces cerevisiae. These are to assess if the human genes can complement the related temperature sensitive yeast IPL1 mutant, which is closely related to AUR1. In addition, fusion constructs containing the N-terminal domain of yeast IPL1 fused to the C-terminal kinase domains of AUR1 and AUR2 were generated. These were produced by insertion of an artificial ClaI site at the 5' end of the kinase domains of the kinases, at the conserved Asp-Asp-Phe-Glu sequence.

Dominant negative AUR1 and AUR2 constructs were also made in both pLXSN and pRK5 by mutation of the invariant Lys (amino acid positions 106 and 162 in AUR1 and AUR2, respectively) to an Met by PCR mutagenesis. The constructs are termed AUR1KM and AUR2KM. Constitutively active forms of AUR1 and AUR2 were generated by mutation of the DNA heading the encoding the phosphorylation site (232 and 288) to an Asp resulting in AUR1TD and AUR2TD.

Expression constructs in both PLXSN and PRK5 were also made containing just the N-terminal, non-catalytic domain of AUR1 and AUR2. These were generated by PCR from the parental constructs and contain the N-terminal 77 amino acids of AUR1 and 132 amino acids of AUR2.

The entire AUR1 and AUR2 open reading frames (no HA-tag) excluding the initiating methionines were generated by PCR and ligated into PGEX vector for bacterial production of GST-fusion proteins for immunization of rabbits for antibody production.

Example 7
Generation of Virus Producing Aurora Cell Lines

To generate high-titer virus stocks, pLXSN recombinant constructs containing either AUR1 or AUR2 genes were transfected into an amphotropic helper cell line PA317 using $CaCl_2$ mediated transfection. After selection on G418, the cells were plated on normal media without G418 (500 ug/ml). Supernatants from resistant cells were used to infect the ecotropic helper cell line GP+E86, and cells again selected on G418. Resistant cells were again taken off G418, and the supernatants harvested every 8–12 hours and pooled as virus stock (Redemann, N., Holzmann, B., Wagner, E. F., Schlessinger, J., & Ullrich, A., Mol. Cell. Biol. 12, 491–498, 1992). Viral stock titers were typically ~$10^6$/ml.

Example 8
Retroviral Infection of NIH-3T3 Cells with Auroras

NIH-3T3, and BALB/3T3 cells were grown in 100 mm plates with DMEM (Gibco) containing 10% fetal calf serum (FCS). The cells were superinfected with the AUR1 and AUR2 retrovirus by adding approximately 3 ml viral supernatant to 15 ml culture media for approximately 24 hours. Cells expressing the retroviral constructs were then selected by growth in DMEM/10% FCS supplemented with 500 ug/ml G418.

Example 9
Generation of Aurora-Specific Immunoreagent

AURORA-specific immunoreagents were raised in rabbits against KLH-conjugated synthetic peptides corresponding to either the N-terminal region of AUR2 ($^{104}$SAPENNPEEQLASK$^{117}$) (SEQ ID NO:22) and ($^{90}$RPLNNTQKSKQPL$^{102}$) (SEQ ID NO:23) or the N-terminus or N-terminal domain of human AUR1 ($^{1}$MAQKENSYPWPYG$^{13}$) (SEQ ID NO:24) and ($^{53}$PGQKVMENSSGTP$^{65}$) (SEQ ID NO:25). Additional immunoreagents were generated by immunizing rabbits with the bacterially expressed full length AUR1 and AUR2 GST-fusion proteins.

Example 10
Transient Expression of Auroras in Mammalian Cells

The pRK5 expression plasmids (10 ug DNA/100 mm plate) containing the HA-tagged AUR1 and AUR2 genes were introduced into COS and 293 cells with lipofectamine (Gibco BRL). After 72 hours, the cells were harvested in 0.5 ml solubilization buffer (20 mM HEPES pH7.35, 150 mM NaCl, 10% glycerol, 1% Triton X-100, 1.5 mM MgCl$_2$, 1 mM EGTA, 2 mM phenylmethylsulfonyl fluoride, 1 μg/ml aprotinin). Sample aliquots were resolved by SDS polyacrylamide gel electrophoresis (PAGE) on 15%acrylamide/0.5% bis-acrylamide gels and electrophoretically transferred to nitrocellulose. Non-specific binding was blocked by preincubating blots in Blotto (phosphate buffered saline containing 5% w/v non-fat dried milk and 0.2% v/v nonidet P-40 (Sigma)), and recombinant protein was detected using a murine Mab to the HA decapeptide tag. Alternatively, recombinant protein can be detected using various AUR1- or AUR2-specific antisera.

Example 11
MYelin Basic Protien is an Artificial Substrate for Aurora1 and Aurora2 Kinase
Method Human colorectal adenocarcinoma SW480 cells were cultured in RPMI 1640 plus 10% fetal bovine serum, L-glutamine, penicillin and streptomycin. Confluent cultures of SW480 cells were washed three times with ice cold phosphate buffered saline (PBS) and then were scraped into 1 ml of ice cold PBS. The cells were centrifuged at 1,000 rpm at 4° C., the PBS aspirated away, and the resulting cell pellet stored at −80° C. The pellets from three 15 cm plates were thawed on ice and resuspended in a total of 1 ml of kinase lysis buffer 50 mM HEPES pH 7.4, 100 mM KCl, 25 mM NaF, 1 mM NaVO$_3$, 0.5% NP40, 1 mM DTT, 2 ug/ml aprotinin, and 1 ug/ml leupeptin) and were rotated gently for 20 minutes at 4° C. The samples were then centrifuged at 10,000×g for 10 minutes at 4° C. and the resulting supernatant was transferred to a clean 1.5 ml centrifuge tube and stored or kept on ice. The protein concentration was determined by Bradford analysis. One milligram of total protein was pre-cleared with 10 μl of protein A-Sepharose (Boehringer) for 15 minutes at 4° C. followed by the addition of 2 μl of either rabbit pre-immune serum, affinity purified auroral peptide antisera, affinity purified auroral peptide antisera plus 6 μg of competing auroral peptide, affinity purified aurora2 peptide antisera, or, affinity purified aurora2 peptide antisera plus 6 μg of competing aurora2 peptide and incubated for 30 minutes at 4° C. Subsequently, 10 μl of protein A-sepharose was added and the incubation was continued for an additional 45 minutes at 4° C. The tubes were briefly centrifuged to pellet the antibody-protein A-sepharose complex and the resulting supernatant was aspirated off. The antibody-protein A-sepharose pellet was washed twice with 0.5 ml of kinase lysis buffer followed by a wash with 0.5 ml of kinase buffer (20 mM HEPES pH 7.4, 125 mM KCl, 10 mM MgCl$_2$, 1 mM NaF, 1 mM NaVO$_3$, and 1 mM DTT). The antibody-protein A-sepharose pellet was resuspended in 20 μl of kinase buffer containing 5 uCi of [γ-32P] ATP and 0.5 mg/ml myelin basic protein (Sigma), incubated for 20 minutes at 37° C. after which 10 μl of protein sample buffer 200 mM Tris-Cl pH 6.8, 40% glycerol, 730 mM B-mercaptoethanol, 0.4% SDS, and 0.05% Bromophenol Blue) was added. The tubes were mixed well and incubated for 5 minutes at 100° C. The samples were resolved on an 18% SDS polyacrylamide gel and visualized by autoradiography.

Results

Aurora1 and aurora2 immunocomplexes were able to phosphorylate myelin basic protein. When competing peptide was used in the immunoprecipitations neither aurora1 nor aurora2 antsera immunocomplexes were able to phosphorylate myelin basic protein more than the pre-immune sera control. This suggests that the kinase activity observed is due to aurora1 and 2 and not to other proteins present in the immunocomplex.

This observation will allow for the purification of active aurora1 and 2 kinase by using myelin basic protein as a substrate to follow kinase activity. It also will allow the development of an in vitro kinase assay using recombinant aurora1 and 2 proteins. Furthermore an aurora1 and 2 in vitro kinase assay will allow one to screen small molecule collections for inhibitors of the aurora1 and 2 kinases by measuring the inhibition of phosphorylation of myelin basic protein.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Those references not previously incorporated herein by reference, including both patent and non-patent references, are expressly incorporated herein by reference for all purposes. Other embodiments are within the following claims.

What is claimed is:

1. An isolated, enriched or purified nucleic acid molecule that encodes at least 100 contiguous amino acids of the amino acid sequence depicted in SEQ ID NO:4.

2. The nucleic acid molecule of claim 1 wherein said molecule encodes at least 200 contiguous amino acids of the amino acid sequence depicted in SEQ ID NO:4.

3. The nucleic acid molecule of claim 1 wherein said molecule encodes at least 300 contiguous amino acids of the amino acid sequence depicted in SEQ ID NO:4.

4. An isolated, enriched or purified nucleic acid molecule comprising the nucleic acid sequence depicted in SEQ ID NO:2.

5. An isolated, enriched or purified nucleic acid molecule comprising (a) a nucleotide sequence that encodes a polypeptide having the amino acid sequence depicted in SEQ ID NO:4, or (b) the complement of the nucleotide sequence of (a).

6. The nucleic acid molecule of claim 1, wherein said nucleic acid molecule differs from the nucleic acid sequence of SEQ ID NO:2, or a fragment thereof, by having no more than 10% base replacements.

7. The nucleic acid molecule of claim 1, wherein said nucleic acid molecule differs from the nucleic acid sequence of SEQ ID NO:2, or a fragment thereof, by having no more than 5% base replacements.

8. An isolated, enriched or purified nucleic acid molecule that encodes at least 100 contiguous amino acids of the amino acid sequence depicted in SEQ ID NO:3.

9. The nucleic acid molecule of claim 8 wherein said molecule encodes at least 200 contiguous amino acids of the amino acid sequence depicted in SEQ ID NO:3.

10. The nucleic acid molecule of claim 8 wherein said molecule encodes at least 300 contiguous amino acids of the amino acid sequence depicted in SEQ ID NO:3.

11. An isolated, enriched or purified nucleic acid molecule comprising the nucleic acid sequence depicted in SEQ ID NO:1.

12. An isolated, enriched or purified nucleic acid molecule comprising (a) a nucleotide sequence that encodes a polypeptide having the amino acid sequence depicted in SEQ ID NO:3, or (b) the complement of the nucleotide sequence of (a).

13. The nucleic acid molecule of claim 8, wherein said nucleic acid molecule differs from the nucleic acid sequence of SEQ ID NO: 1, or a fragment thereof, by having no more than 10% base replacements.

14. The nucleic acid molecule of claim 8, wherein said nucleic acid molecule differs from the nucleic acid sequence of SEQ ID NO: 1, or a fragment thereof, by having no more than 5% base replacements.

15. A nucleic acid probe for the detection of nucleic acid encoding an AUR-2 polypeptide in a sample, the complement of said probe able to encode at least 100 contiguous amino acids of the amino acid sequence depicted in SEQ ID NO:4.

16. A nucleic acid probe for the detection of nucleic acid encoding an AUR-1 polypeptide in a sample, the complement of said probe able to encode at least 100 contiguous amino acids of the amino acid sequence depicted in SEQ ID NO:3.

17. A recombinant molecule comprising a nucleic acid molecule of any one of claims 1, 2, 3, 4, 5, 6 or 7.

18. A recombinant molecule comprising a nucleic acid molecule of any one of claims 8, 9, 10, 11, 12, 13 or 14.

19. An expression vector comprising a nucleic acid molecule of any one of claims 1, 2, 3, 4, 5, 6 or 7 operably linked to a regulatory nucleotide sequence that controls expression of the nucleic acid in a host cell.

20. An expression vector comprising a nucleic acid molecule of any one of claims 8, 9, 10, 11, 12, 13 or 14 operably linked to a regulatory nucleotide sequence that controls expression of the nucleic acid in a host cell.

* * * * *